United States Patent [19]

Machatzke

[11] 4,008,222

[45] Feb. 15, 1977

[54] ANTHRAQUINONE DYESTUFFS

[75] Inventor: Heinz Machatzke, Leverkusen, Germany

[73] Assignee: Bayer Aktiengesellschaft, Leverkusen, Germany

[22] Filed: Dec. 16, 1966

[21] Appl. No.: 602,140

[52] U.S. Cl. .............. 260/239.3 T; 260/239.3 R; 260/326 D; 260/304 A; 260/372; 260/301; 260/377; 260/380; 260/293.62; 260/326.5 FM; 260/250 P; 260/250 Q; 260/347.3; 260/295 T; 260/307.5; 8/39 B; 8/39 C

[51] Int. Cl.$^2$ .............. C07D 223/10; C07C 49/95

[58] Field of Search ......... 260/326.5, 326.3, 239.3, 260/377, 380, 372, 304, 326 D, 371

[56] References Cited

UNITED STATES PATENTS

| | | | |
|---|---|---|---|
| 2,559,787 | 7/1951 | Olpin et al. | 260/377 |
| 2,888,467 | 5/1959 | Richter | 260/379 |
| 2,957,884 | 10/1960 | Moergeli | 260/377 |
| 3,123,638 | 3/1964 | Schaeffer | 260/562 |
| 3,236,843 | 2/1966 | Straley et al. | 260/380 |
| 3,274,198 | 9/1966 | Turetzky | 260/377 |
| 3,320,287 | 5/1967 | Schwander | 260/377 |
| 3,433,835 | 3/1969 | Muller et al. | 260/562 O |
| 3,497,527 | 2/1970 | Randall et al. | 260/239.3 |

Primary Examiner—Natalie Trousof
Attorney, Agent, or Firm—Plumley and Tyner

[57] ABSTRACT

Anthraquinone dyestuffs suitable for use in dyeing and printing synthetic fiber material, particularly polyesters, and process for their preparation which comprises reacting an anthraquinone which contains, in at least one β-position, a reactive group which will come off, with a phenol, an alcohol, an aromatic or aliphatic mercaptan or amine which contains an aryl radical substituted by at least 1 acylamino methylene group or an anthraquinone which contains, in at least one β-position, an aryl radical attached directly or through a bridge with a methylolamide or a derivative thereof or an equivalent amount of a mixture of formaldehyde or formaldehyde-yielding compound and an aliphatic or aromatic nitrile or the amide or imide derived therefrom.

8 Claims, No Drawings

ANTHRAQUINONE DYESTUFFS

This invention comprises new and valuable anthraquinone dyestuffs, and the production and use of the same.

The new anthraquinone dyestuffs according to the invention are free from sulphonic acid groups and are obtainable when anthraquinones which contain in at least one β-position a reactive group which comes off (leaving group) are reacted with phenols, alcohols, aromatic or aliphatic mercaptans or amines which contain an aryl radical which is substituted by at least one acylaminomethylene group, or when anthraquinones which contain in at least one β-position an aryl radical which may be attached via a bridge member are reacted either with methylolamides or derivatives thereof or with equivalent amounts of a mixture of formaldehyde (or compounds which split off formaldehyde) and aliphatic or aromatic nitriles (which are free from sulphonic acid groups) or the amides or imides derived therefrom.

The anthraquinones used according to the invention may contain further substituents in the anthraquinone radical. In the part of the anthraquinone that contains or will contain the aryl radical which is in β-position and will bear an acylaminomethylene group, the anthraquinones preferably contain in one or preferably both α-positions a hydroxy, alkoxy, an aliphatic or aromatic thioether group or an amino group which may be substituted by e.g. hydrocarbon radicals.

The anthraquinones may, of course, additionally contain further substituents, preferably the α-positions being substituted by e.g. hydroxy, alkoxy, arylmercapto, alkylmercapto groups, amino or nitro groups which may possibly by further substituted, or halogen.

The external phenyl radical in β-position may be attached to the anthraquinone nucleus directly or via a bridge member, as for example via an —O—, —S—, —NH—, —O—alkylene—, —S—alkylene—, —O—alkylene—O—, —S—alkylene—O—, —O—alkylene—S— or —S—alkylene—S— bridge. The phenyl radical may, in addition, contain other substituents, such as e.g. alkyl, alkoxy, halogen, cyano, mercapto or alkylmercapto groups which may be contained once or several times in the phenyl radical.

The acylaminomethylene group which substitutes the external phenyl radical in β-position may be any acylamino group which should not, however, contain a labile aliphatic halogen atom. The acyl radicals contain preferably up to 18 carbon atoms.

The anthraquinones may also contain the acylaminomethylenephenyl radical more than once in a β-position.

Examples of anthraquinones which contain in β-position a reactive group which comes off, such as e.g. halogen such as chlorine bromine or sulphonic acid groups or aryloxy groups, e.g. as phenoxy group, are as follows:

11-amino-4-hydroxy-2-bromo- or 2-chloro-anthraquinone, 1,4-diamino-2,3-dichloro-anthraquinone, 1,8-diamino-4, 5-dihydroxy-2-bromo- or 2-chloro-anthraquinone, 1,4-diamino-2-bromo- or 2-chloro-anthraquinone, 1-amino-4-phenylamino-2-chloro-anthraquinone, 1,4-diamino-5-nitro-2-bromo-anthraquinone, 1-amino-4-hydroxy-anthraquinone-2-sulphonic acid, 1,4-diamino-anthraquinone-2-sulphonic acid or 1,5-dihydroxy-4,8-diamino-anthraquinone-2-sulphonic acid, 1-amino-2-phenoxy-4-hydroxy-anthraquinone.

Examples of anthraquinones which contain in β-position an aryl radical which may possibly be attached via a bridge member are as follows:

1-amino-4-hydroxy-2-phenoxy-anthraquinone, 1-amino-4-hydroxy-2-(4'-methylphenoxy)-anthraquinone, 1-amino-4-hydroxy-2-(4'-methoxyphenoxy)-anthraquinone, 1-amino-4-hydroxy-2-(4'-methylmercaptophenoxy)-anthraquinone, 1-amino-4-hydroxy-2-(2',4'-dimethylphenoxy)-anthraquinone, 1-amino-4-hydroxy-2-(4'-isopropylphenoxy)-anthraquinone, 1-amino-4-hydroxy-2-(3'-methylphenoxy)-anthraquinone, 1-amino-4-hydroxy-2-(4'-hydroxy-phenoxy)-anthraquinone 1-amino-4-hydroxy-2-(2'-chlorophenoxy)-anthraquinone, 1-amino-4-hydroxy-2-benzyloxyanthraquinone, 1-amino-4-hydroxy-2phenoxy-ethoxy-anthraquinone, 1-amino-4-hydroxy-2-phenylmercapto-anthraquinone, 1-amino-4-hydroxy-2-benzylmercapto-anthraquinone, 1-amino-4-hydroxy-2-phenylmercaptoethoxy-anthraquinone, 1-amino-4-hydroxy-2-phenylethoxy-anthraquinone 1-amino-4-hydroxy-2-(4'-methoxy-phenylethoxy)-anthraquinone, 1-amino-4-hydroxy-2-(4'-hydroxy-phenyl)-anthraquinone, 1-amino-4-hydroxy-4-ethoxyphenyl-anthraquinone, 1,4-diamino-2-phenoxy-3-chloro-anthraquinone, 1,4-diamino-2,3-diphenoxy-anthraquinone, 1,4-diamino-2-(4'-methylphenoxy)-3-phenoxy-anthraquinone, 1,4-diamino-2-(3'-methoxyphenylsulphonyl)-anthraquinone, 1,4-diamino-2-(3'-methoxyphenylsulphoxyl)-anthraquinone, 1-amino-4-hydroxy-2-phenylamino-anthraquinone, 1,4-diamino-2-phenoxy-3-hydroxyethylmercapto-anthraquinone, 1,5-dihydroxy-4,8-diamino-2-(4'-methoxyphenyl)-anthraquinone, 1,5-dihydroxy-4,8-diamino-2-(4'-ethoxyphenyl)-anthraquinone, 1-amino-5-nitro-4,8-dihydroxy-3-(4'-methoxyphenyl)-anthraquinone, 1,5-dihydroxy-4,8-diamino-3-phenoxy-anthraquinone, 1,4-diamino-5-nitro-2-phenoxy-anthraquinone, 1,5-dihydroxy-4,8-diamino-3-(4'-methoxyphenyl)-anthraquinone, 1,4-diamino-5,8-dihydroxy-2-phenoxy-anthraquinone, 1,5-dihydroxy-4,8-diamino-2-chloro-3-phenoxy-anthraquinone, 1-amino-4-phenylamino-2-phenoxy-anthraquinone,1,4-dihydroxy-2-phenoxy-anthraquinone, 1-amino-2-benzylamino-4-hydroxy-anthraquinone, 1,4-dihydroxy-2-phenylmercapto-anthraquinone.

As examples of the phenols, alcohols, aromatic or aliphatic mercaptans or amines which contain an aryl radical which is substituted by an acylaminomethylene group, the following are mentioned:

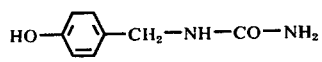

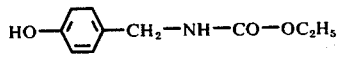

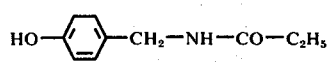
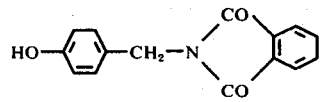
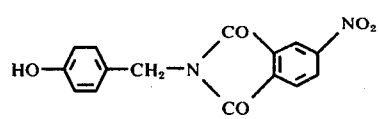
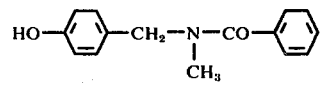
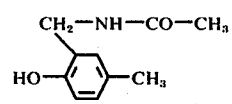
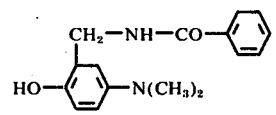
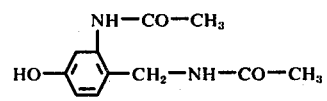
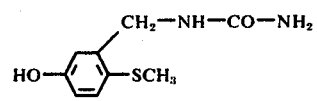
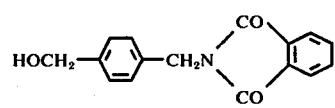
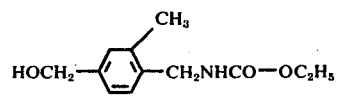
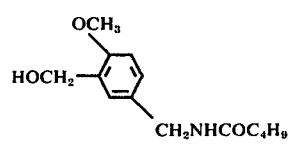
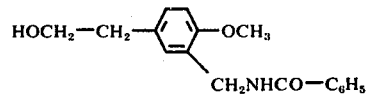
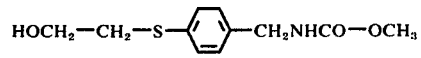
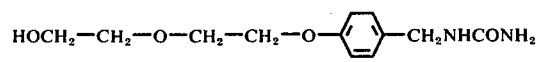
-continued
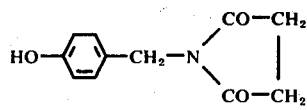
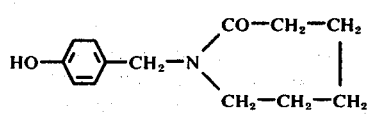
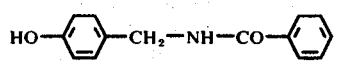
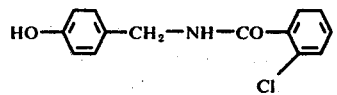
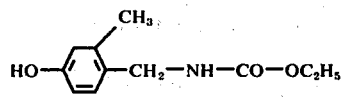
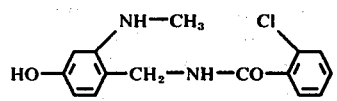
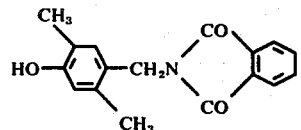
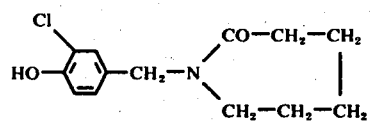
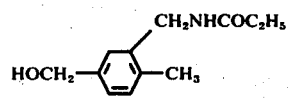
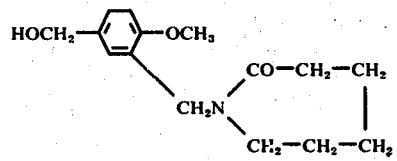
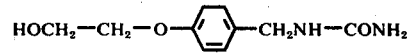

-continued
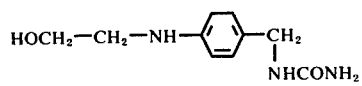
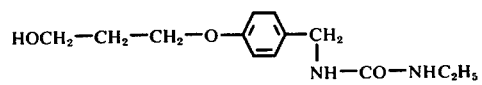
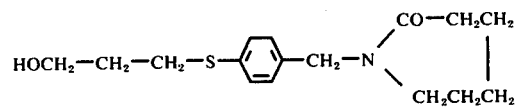
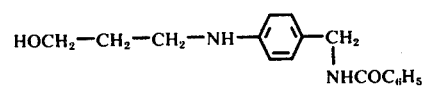
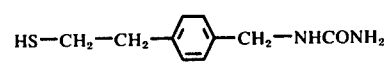
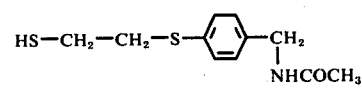
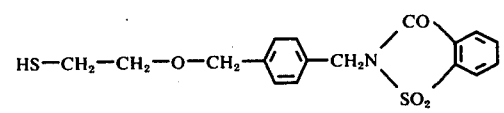
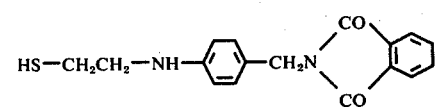
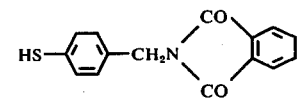
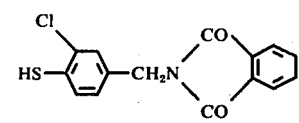
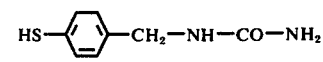
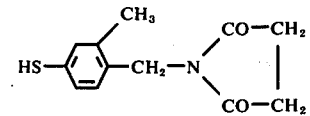
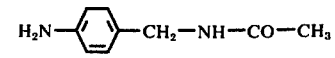
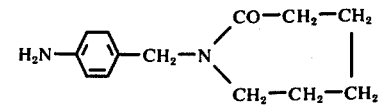
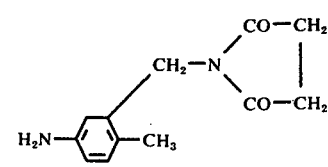
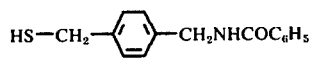
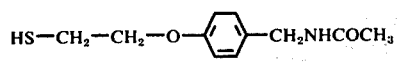
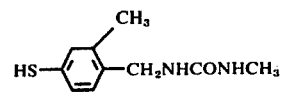
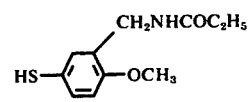
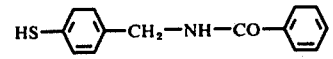
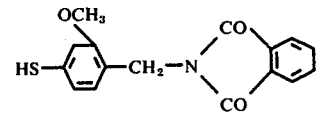
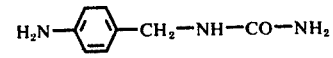
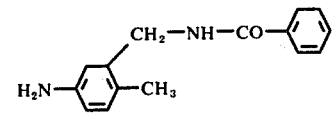
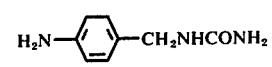

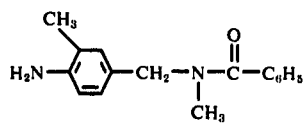

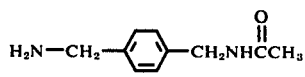

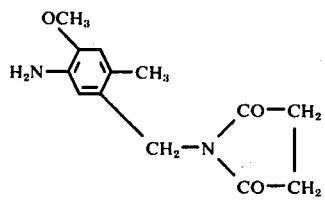

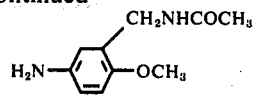

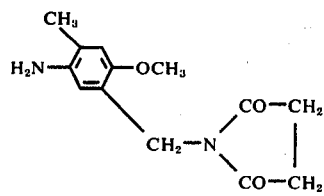

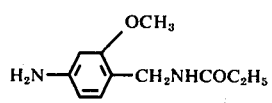

The following compounds are examples of the methylol compounds or derivatives thereof, in particular the lower methylol ethers or the corresponding halomethylamides, which are reacted with the anthraquinones which are substituted in β-position by an aryl radical which may possibly be attached via a bridge member:

HOCH$_2$—NH—COCH$_3$, HOCH$_2$—NH—COC$_2$H$_5$, CH$_3$OCH$_2$—NHCOC$_3$H$_5$, HOCH$_2$—NHCOC$_4$H$_9$, HOCH$_2$—NHCOC$_5$H$_{11}$, CH$_3$OCH$_2$—NHCOH,

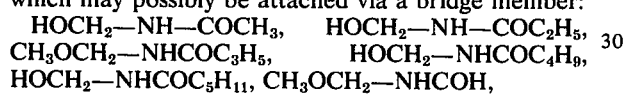

HOCH$_2$—NH—CO(CH$_2$)$_9$—CH$_3$, HOCH$_2$—NH—CO—C$_{17}$H$_{35}$, HOCH$_2$—NH—COCH$_2$OH,

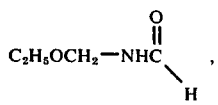

HOCH$_2$—NH—COCH$_2$—OCH$_3$, HOCH$_2$—NH—COCH$_2$—O—SO$_2$CH$_3$

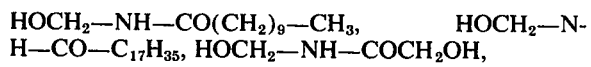

HOCH$_2$—NHCOCH$_2$—SCH$_3$,

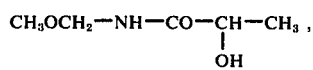

HOCH$_2$—NHCO—CH$_2$CH$_2$—O—SO$_2$CH$_3$, HOCH$_2$—NH—COCH$_2$CH$_2$—SO$_2$CH$_3$, HOCH$_2$—NH—COCH$_2$NH$_2$, HOCH$_2$—NHCOCH$_2$CH$_2$NH$_2$,

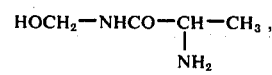

CH$_3$OCH$_2$—NH—COCH=CH$_2$, HOCH$_2$—NH—COCH$_2$CH(CH$_3$)$_2$,

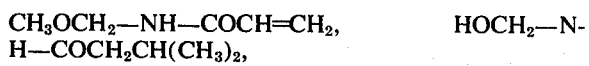

HOCH$_2$—NH—CO—CH=CH—CH$_3$, HOCH$_2$—NH—CO—CH$_2$—CH=CH$_2$ HOCH$_2$—NH—CO—CH$_2$—NH-COCH$_2$—C$_6$H$_5$, HOCH$_2$—NH—CO—CH$_2$—C$_6$H$_5$, HOCH$_2$—NH—COCH$_2$—COOH, HOCH$_2$—NH—CO(CH$_2$)$_2$COOH, HOCH$_2$—NH—CO(CH$_2$)$_4$COOH, HOCH$_2$—NH—CO—(CH$_2$)$_8$CH=CH$_2$,

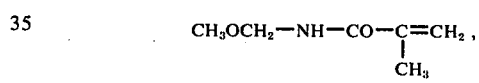

HOCH$_2$—NH—CO(CH$_2$)$_2$—CONH$_2$, CH$_3$OCH$_2$—NH—CO—OCH$_3$, HOCH$_2$—NH—CO—O—C$_2$H$_5$, CH$_3$OCH$_2$—NH—CO—NH$_2$, HOCH$_2$—NH—CONH$_2$,

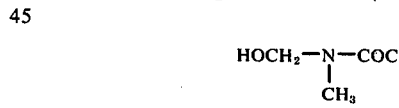

CH$_3$OCH$_2$—NH—CON(CH$_3$)$_2$, CH$_3$OCH$_2$—NH—CO—NH—C$_6$H$_5$, HOCH$_2$—NH—CO—C$_6$H$_5$,

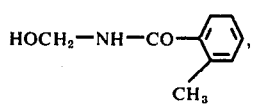

-continued
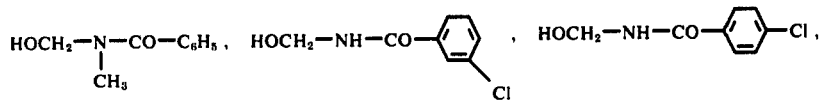
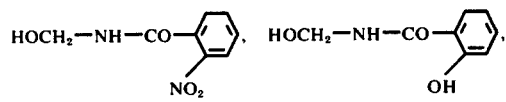
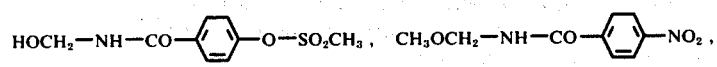
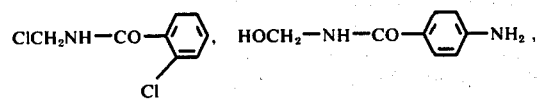
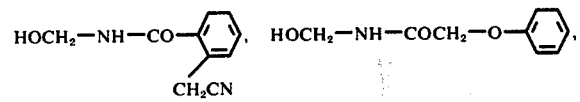
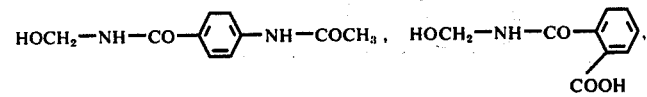
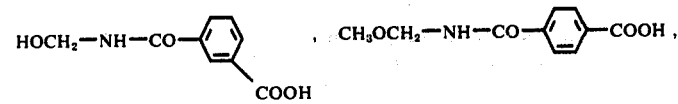
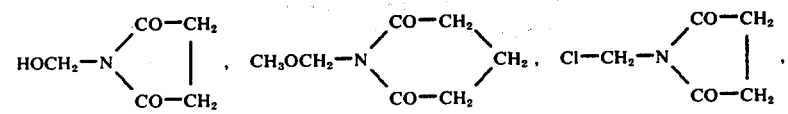
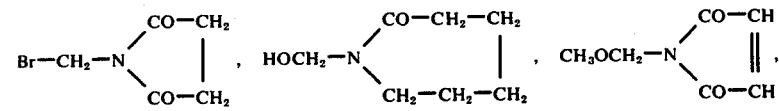
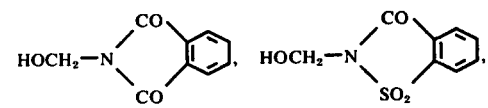
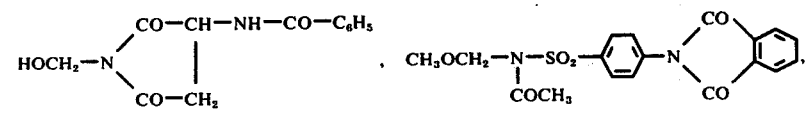
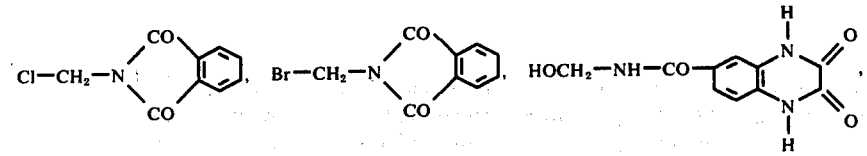
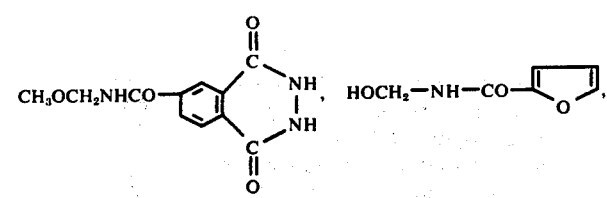
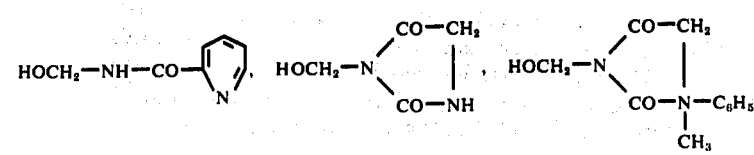

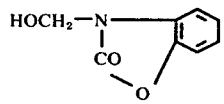

Examples of the aliphatic or aromatic nitriles or the corresponding amides or imides which are used in an embodiment of the process are the following compounds: $CH_3CN$, $C_2H_5CN$, $C_5H_{11}CN$, $CH_2=CH-CN$,

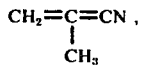

$C_6H_5CN$, $CH_3CONH_2$, $C_2H_5-CONH_2$, $C_3H_7CONH_2$, $H_2NCONH_2$,

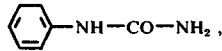

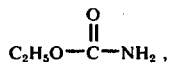

$(CH_3)_2NH-CO-NH_2$,

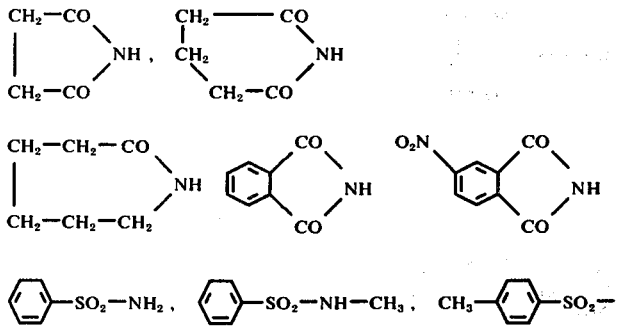

The reaction of the reaction components can take place e.g. at temperatures in the range from 0° to 100° C, preferably 0° to 60° C. The reaction of the methylol compounds or their derivatives or of the formaldehyde mixtures with the anthraquinones which contain an external aryl radical takes place expediently in the presence of a strongly acid condensation agent, such as e.g. 80 to 100% sulphuric acid, 90 to 100% phosphoric acid, glacial acetic acid/hydrochloric acid mixtures or sulphuric acid/formic acid mixtures.

The new anthraquinone dyestuffs obtained according to the invention are particularly well suited for the dyeing and printing of polyester materials. They can also be used for the dyeing and printing of synthetic polyamide fibres or of wool and silk. Their dyeings on polyester materials are distinguished by very good fastness to light and outstanding fastness to sublimation. The dyeings, in particular on polyester materials, possess a very good substantivity.

Dyestuffs which are particularly well suited for dyeing on to polyester materials and which are obtained according to the process according to the invention can be characterised by the following formula:

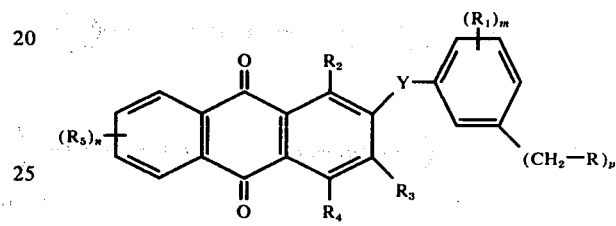

wherein Y stands for a direct bond or a bridge member such as —O—, —S—, —NH—, —O—alkylene, —S—alkylene—, —O—alkylene—O—, O—alkylene—N, —S—alkylene—O—or —S—alkylene-S-, R denotes a (possibly further substituted) acylamino group, the radicals $R_1$ to $R_5$ may stand for hydrogen or further substituents such as hydroxy, alkoxy, nitro or amino groups or halogen, and $m$, $n$, and $p$ stand for 1 to 3.

EXAMPLE 1

330 Parts 1-amino-2-phenoxy-4-hydroxyanthraquinone are introduced at a temperature of 0° to 5° C into 2500 parts 96% sulphuric acid and then 200 parts N-methylolphthalimide are added at 0° to 10° C. Stirring is effected for 3 hours at 5° to 10° C and then for a further 20 hours at 20° C. The mixture is now discharged into 10,000 parts ice and this is followed by filtering off with suction, washing neutral, and drying at 60° C in a drying cabinet; there are obtained 480 parts of the dyestuff of the constitution

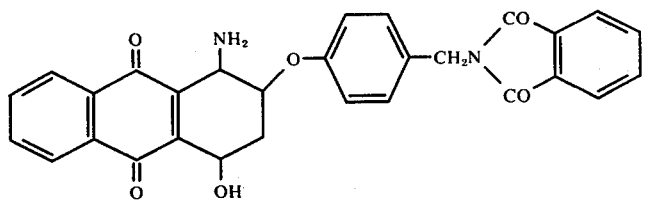

which dyes polyester fibre fabric in pink shades and is distinguished by outstanding fastness to light and sublimation.

EXAMPLES 2 to 33

When the procedure described in Example 1 is followed but using instead of the anthraquinone dyestuff named there equivalent amounts of those stated in Table 1, column 2, and, instead of the N-methylolphthalimide used above, equivalent amounts of the methylolamides stated in column 3, there are obtained further valuable anthraquinone dyestuffs which contain the respective acylaminomethylene group in the position indicated in column 4.

Table 1

| Example No. | Starting product | | | | Methylol compound used | Reaction product obtained Position of the acylamino-methylene group | Red Shade |
|---|---|---|---|---|---|---|---|
| | Z | $X_1$ | $X_2$ $X_3$ | $X_4$ | | | |
| 2 | OH | H | H H | H | $HOCH_2NHCOCH_3$ | $X_3$ | red |
| 3 | OH | H | H H | H | $HOCH_2NHCOC_5H_{11}$ | $X_3$ | red |
| 4 | OH | H | H H | H | $HOCH_2NHCO-OC_2H_5$ | $X_3$ | red |
| 5 | OH | H | H H | H | $CH_3OCH_2NHCO-OC_2H_5$ | $X_3$ | red |
| 6 | OH | H | H H | H | $CH_3OCH_2NHCONH_2$ | $X_3$ | red |
| 7 | OH | $CH_3$ | H H | H | $CH_3OCH_2NHCONH_2$ | $X_3$ | red |
| 8 | OH | $CH_3$ | H $CH_3$ | H | $CH_3OCH_2NHCONH_2$ | $X_5$ | red |
| 9 | OH | H | H H | H | $EOCH_2NHCO-C_6H_5$ | $X_3$ | red |
| 10 | OH | H | H H | H | $HOCH_2NHCO-\langle\text{phenyl}\rangle-Cl$ | $X_3$ | red |
| 11 | OH | H | H H | H | $CH_3OCH_2NHCO-\langle\text{o-Cl-phenyl}\rangle$ | $X_3$ | red |
| 12 | OH | H | H $OCH_3$ | H | $CH_3OCH_2NHCO-\langle\text{o-Cl-phenyl}\rangle$ | $X_2$ | red |
| 13 | OH | H | H H | H | $HOCH_2N(CO)_2\text{-phenyl}$ (phthalimide) | $X_3$ | red |
| 14 | OH | H | H H | H | $HOCH_2N(COCH_2CH_2)(CH_2CH_2CH_2)$ | $X_3$ | red |
| 15 | OH | H | H $CH_3$ | H | $HOCH_2N(COCH_2CH_2)(CH_2CH_2CH_2)$ | $X_1$ | red |
| 16 | OH | H | H $C_3H_7$ | H | $HOCH_2N(COCH_2CH_2)(CH_2CH_2CH_2)$ | $X_1$ | red |
| 17 | OH | H | H H | H | $CH_3OCH_2N(CO)_2\text{-phenyl}$ | $X_3$ | red |
| 18 | OH | H | H H | H | $ClCH_2N(CO)_2\text{-phenyl}$ | $X_3$ | red |

Table 1-continued

[Structure: 1-amino-anthraquinone with NH2, O-phenyl ring bearing X1, X2, X3, X4, X5=H, and Z at position 4]

| Example No. | Starting product Z | X₁ | X₂ | X₃ | X₄ | Methylol compound used | Reaction product obtained Position of the acylaminomethylene group | Red Shade |
|---|---|---|---|---|---|---|---|---|
| 19 | OH | Cl | H | H | H | ClCH₂N(CO-)(CO-)C₆H₄ (phthalimide-type) | X₃ | red |
| 20 | OH | H | H | H | H | HOCH₂N(COCH₂-)(COCH₂-) | X₃ | red |
| 21 | OH | H | H | H | H | HOCH₂N(CO-)(SO₂-)C₆H₄ | X₃ | red |
| 22 | OH | H | H | H | H | HOCH NHCO—C₆H₄—COOH | X₃ | red |
| 23 | NH₂ | H | H | H | H | CH₃OCH₂NHCONH₂ | X₃ | red |
| 24 | NH₂ | H | H | H | H | CH₃OCH₂NHCONHC₂H₅ | X₃ | red |
| 25 | NH₂ | H | H | H | H | HOCH₂NHCOC₂H₅ | X₃ | red |
| 26 | NHCH₃ | H | H | H | H | HOCH₂NHCOC₂H₅ | X₃ | red |
| 27 | NHC₆H₅ | H | H | CH₃ | H | HOCH₂NHCOC₆H₅ | X₁ | red |
| 28 | NHCOCH₃ | H | H | H | H | HOCH₂NHCOCH₃ | X₃ | red |
| 29 | NH₂ | H | H | H | H | HOCH₂N(COCH₂CH₂-)(CH₂CH₂CH₂-) | X₃ | red |
| 30 | NH₂ | H | H | H | H | HOCH₂N(CO-)(CO-)C₆H₄ | X₃ | red |
| 31 | NH₂ | H | H | H | H | HOCH₂N(CO-)(SO₂-)C₆H₄ | X₃ | red |
| 32 | NH—SO₂—C₆H₅ | H | H | H | H | HOCH₂NHCOCH₃ | X₃ | red |
| 33 | NH—SO₂—C₆H₄—CH₃ | H | H | H | H | CH₃OCH₂NHCONH₂ | X₃ | red |

EXAMPLE 34 a. 422 Parts 1,4-diamino-2,4-diphenoxyanthraquinone are introduced at 0° to 5° c into 3000 parts 96% sulphuric acid and then 95 parts N-methylolmethylurethane are added at 0° to 10° C. Stirring is effected for 4 hours at 5° to 10° C and then for a further 20 hours at 20° C. The mixture is discharged into 12000 parts ice and this is followed by filtering off with suction, washing neutral, and drying at 60° C in a drying cabinet; there are obtained 430 parts of the dyestuff of the constitution

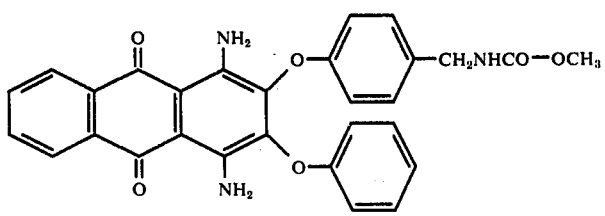

which dyes polyester fibre fabrics blue-violet and possesses outstanding fastness to sublimation.

b. Corresponding dyestuffs are obtained when the procedure described in Example 34(a) is followed but using instead of the N-methylolmethylurethane used there equivalent amounts of the following methylolamides:

N-methylolbenzamide, N-methylolsuccinic acid imide, N-methylophthalimide, N-methylol-ε-caprolactam and N-methylolmaleic acid imide.

EXAMPLE 35 a. 375 parts 1-amino-2-(2'-phenoxyethoxy)-4-hydroxyanthraquinone are dissolved at 0° to 5° C in 2000 parts 85% sulphuric acid. 120 parts N-methylolsuccinic acid imide are then added, stirring is effected for 20 hours at 0° to 5° C and the mixture is then discharged into 10000 parts ice. This is followed by filtering off with suction, washing neutral, and drying at 60° C in a drying cabinet; there are obtained 470 parts of a dyestuff of the constitution

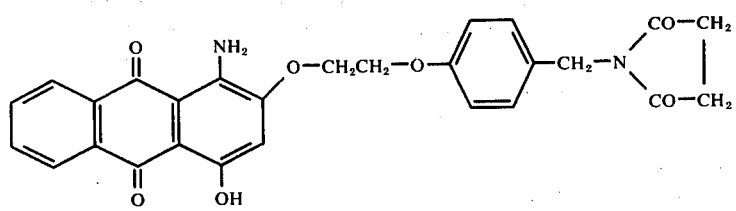

which dyes polyester fibre fabric in red shades with outstanding fastness to sublimation.

B. When the procedure described in Example 35(a) is followed but using instead of the N-methylolsuccinic acid imide used there equivalent amounts of the following methylolamides, there are obtained corresponding dyestuffs with excellent fastness:

methylolacetamide, methylolethylurethane, methylolphthalimide, methylolmaleic acid amide and monomethylolsuccinic acid imide.

EXAMPLE 36

A polyester fibre fabric is impregnated on a padding mangle with a liquor which contains 20 parts of the finely dispersed dyestuff mentioned in Example 1 and 10 parts of a thermosol auxiliary. The fabric is squeezed off, dried at 80° to 120° C and treated at 190° to 220° C within 45 seconds with hot air. It is then rinsed, washed and dried. A red dyeing is obtained which is distinguished br very good light-fastness and outstanding fastness to sublimation.

EXAMPLE 37

20 parts of a polyester fibre are dyed for 1.5 hours at 100° C and pH 4.5 in a liquor which in 800 parts water contains 0.2 parts of the finely dispersed dyestuff mentioned in Example 1 and 3 parts o-cresotic acid methyl ester. After washing and drying, a red dyeing of very good light-fastness and outstanding fastness to sublimation is obtained.

EXAMPLE 38 a. 348 Parts 1-amino-2-mercaptophenyl-4-hydroxyanthraquinone are introduced at a temperature of 0° to 5° C into 2500 parts 96% sulphuric acid and then 130 parts monomethoxymethylurea are added. Stirring is effected for 3 hours at 5° to 10° C and then for a further 20 hours at room temperature. The mixture is now discharged into 10000 parts ice and this is followed by filtering off with suction, washing neutral, and drying at 60° C in a drying cabinet. There are obtained 440 parts of the dryestuffs of the constitution

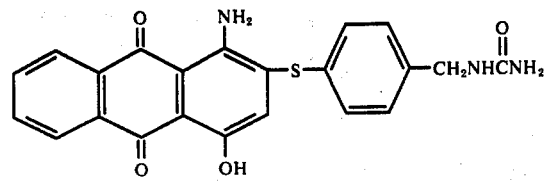

which dyes polyester fabric violet and is distinguished by very good fastness to sublimation.

b. When the procedure described in Example 38(a) is followed but using instead of the monomethoxymethylurea mentioned there equivalent amounts of the following methylol compounds, further valuable anthraquinone dyestuffs fast to sublimation are obtained:

N-methylolacetamide, N-methylolbenzamide, N-methylolphthalimide, N-methylolethylurethane, N-methylol-ε-caprolactam and N-methylolsuccinic acid imide.

EXAMPLE 39

346 Parts 1,5-dihydroxy-4,8-diamino-2-(4'-methoxyphenyl)anthraquinone are dissolved at 0° to 5° C in 3000 parts 96% sulphuric acid and then 150 parts N-methylolethylurethane are added. Stirring is effected, first for 3 hours at 5° to 15° C and then for a further 20 hours at 20 to 25° C. The mixture is discharged into 10000 parts ice and this is followed by filtering off with suction, washing neutral, and drying at 60° C in a drying cabinet. There are obtained 440 parts of the dyestuff of the constitution

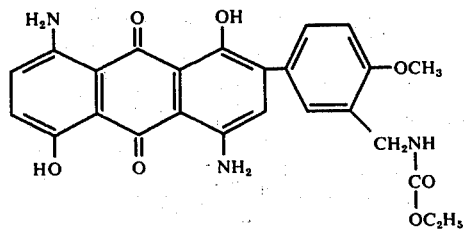

which dyes polyester fabric blue and is distinguished by very good fastness to sublimation.

EXAMPLE 40

345 Parts 1-amino-2-oxybenzyl-4-hydroxyanthraquinone are dissolved in 2800 parts 90% sulphuric acid, and 155 parts N-methylol-ε-caprolactam are added at 0° to 5° C. The mixture is stirred for 24 hours at 0° to 5° C and discharged into 10000 parts ice; the precipitated dyestuff is filtered off with suction and dried at 60° C. There are obtained 450 parts of the dyestuff of the constitution

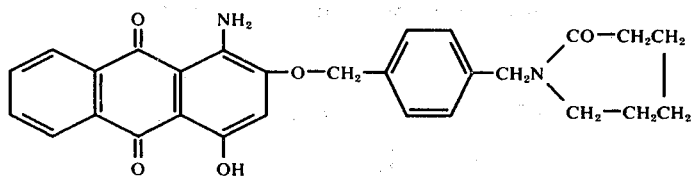

which dyes polyester fibres in red shades and is distinguished by very good fastness to sublimation.

EXAMPLE 41

10 Parts of the dyestuff obtainable according to Table 1 (Example 6) of the constitution

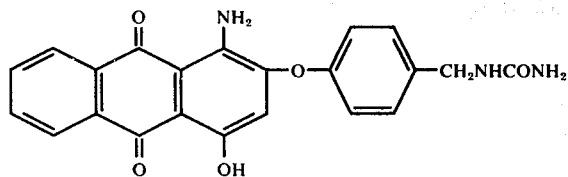

are ground with 10 parts of a naphthalene-formaldehyde condensation product and stirred into 10000 parts water of pH 6. 10 Parts of a levelling auxiliary, e.g. an alkylphenylpolyglycol ether, are now added. 10000 parts of a synthetic polyamide fibre material are introduced into this dyebath and the temperature is slowly increased to 100° C. After dyeing has been effected for 1 hour at this temperature, the fibre material is rinsed, washed and dried. A red dyeing with good fastnesses to light and washing is obtained.

EXAMPLE 42

214 Parts 1-amino-2-bromo-4-hydroxyanthraquinone are added to a solution of 200 parts N-(4'-mercaptobenzyl)-ε-caprolactam and 63 parts potassium hydroxide in 400 parts ethanol and the mixture is heated for 8 hours under reflux. The precipitated reaction product if filtered off cold with suction, washed neutral, and dried at 60° C; there are obtained 310 parts of the dyestuff of the constitution

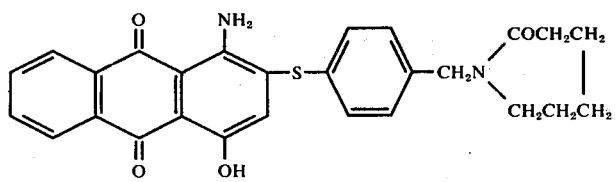

which dyes polyester fibres violet with very good fastnesses to washing and very good fastness to sublimation.

When the procedure described in Example 42 is followed but using instead of N-(4'-mercaptobenzyl)-ε-caprolactam equivalent amounts of N-(4'-mercaptobenzyl)-ethylurethane, N-(4'-mercaptobenzyl)-acetamide or N-(4'-mercaptobenzyl)-phthalimide, further dyestuffs with very good fastnesses to washing, light and sublimation are obtained.

EXAMPLE 43

300 Parts N-(3'-chloro-4'-hydrobenzyl)-phthalimide, 50 parts 1-amino-2-bromo-4-hydroxyanthraquinone and 25 parts potassium hydroxide are mixed, and heated to 145° C for 9 hours. The mixture is put into water, acidified, and filtered off with suction. Drying is effected at 70° C, the dry mixture is extracted several times with methylene chloride and 48 parts of the dyestuff of the constitution stated in Table 1, Example 19, are obtained.

EXAMPLE 44

20 Parts 1-amino-2-(4'-chlorophenoxy)-4-hydroxyanthraquinone and 100 parts N-(4'-aminomethylenebenzyl)-ε-caprolactam are heated to 130° to 140° C for 5 hours. The melt is then poured into water, filtering off with suction is effected and the dyestuff obtained is washed with ethanol. There are obtained 22 parts of the dyestuff of the constitution.

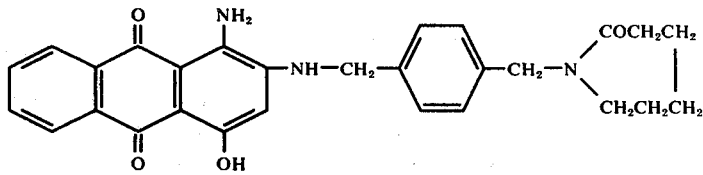

which dyes polyester materials bluish-red in good fastnesses.

EXAMPLE 45

30 Parts 1-amino-2-(2'-phenylethoxy)-4-hydroxyanthraquinone are dissolved at 0° to 5° C in 300 parts 90% sulphuric acid. 15 Parts N-methylol-ε-caprolactam are now introduced within 30 minutes and stirring is effected for a further 20 hours at 0° to 10° C. The mixture is then discharged into ice and this is followed by filtering off with suction and washing acid-free; after drying, there are obtained 35 parts of the dyestuff of the constitution

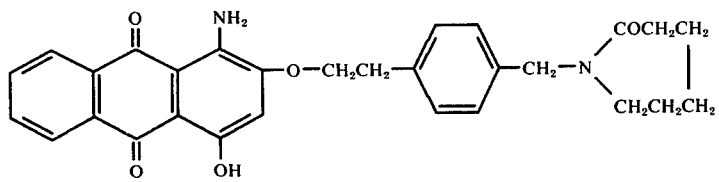

which dyes polyester fabric in red shades with very good fastnesses to light, washing and sublimation.

EXAMPLE 46

33.2 Parts 1,4-dihydroxy-2-phenoxyanthraquinone are introduced at 5° to 15° C into 350 parts 96% sulphuric acid, and 30 parts N-methylol-ε-caprolactam are added. Stirring is continued for a further 10 hours at room temperature and the mixture is discharged into ice and this is followed by filtering off with suction and washing neutral; after drying, there are obtained 44 parts of the dyestuff of the constitution

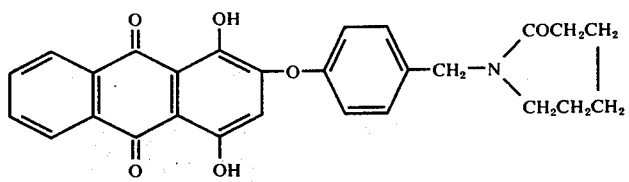

which dyes polyamide fabric in orange-red shades with very good fastnesses to washing and light.

When the procedure in Example 46 is followed but using instead of 30 parts N-methylol-ε-caprolactam equivalent amounts of e.g. the following methylol compounds, further dyestuffs with very good fastness are obtained:

methylolacetamide, methylolbenzamide, methylolphthalimide, methylolmethylurethane, methylolethylurethane, methylolsuccinic acid imide, methoxymethylurea and methoxymethyldimethylurea.

EXAMPLE 47

36 Parts 1,4-dihydroxy-2-phenylmercaptoanthraquinone are dissolved at 0° to 5° C in 450 parts 98% sulphuric acid. 40 Parts of a 76% methylolacetamide solution are added dropwise within 30 minutes at a temperature of, at the maximum, 10° C, and stirring is then continued for a further 15 hours at 15° hours at 20° C. The mixture is discharged into ice; the precipitated dyestuff is filtered off with suction, washed neutral and, after drying, there are obtained 45 parts of a dyestuff of the constitution

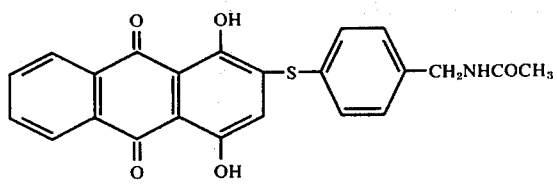

which dyes polyester fabric is yellowish-red shades with very good fastnesses.

When the procedures described in Example 47 is followed but, instead of the methylol compound used therein, there is used e.g. that stated in Example 46, further dyestuffs with very good fastnesses are obtained.

EXAMPLE 48

40 Parts 1,4-dihydroxy-2-mercaptobenzylanthraquinone are dissolved at 5° to 15° C in 450 parts 90% sulphuric acid. 18 Parts methylolphthalimide are added, stirring is continued for further hours at 10° to 15° C until the alkylation is complete, and the mixture is then discharged into ice. The precipitated dyestuff is filtered off with suction, washed neutral and dried; there are obtained 46 parts of the dyestuff of the constitution

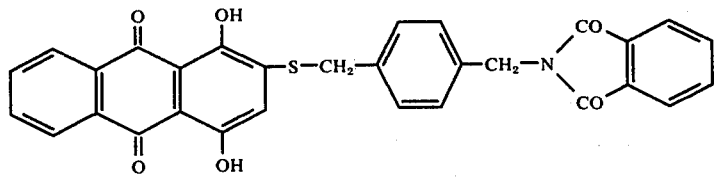

which dyes polyester materials in red shades with very good fastnesses.

EXAMPLE 49

35 Parts 1,4,5,8-tetrahydroxy-2-phenoxyanthraquinone are dissolved at 5° to 10° C in 450 parts 96% sulphuric acid. 18 parts methylolethylurethane are added, stirring is effected for 18 hours at room temperature and the mixture is then discharged into ice. The precipitated dyestuff is filtered off with suction, washed neutral and dried; there are obtained 38 parts of the dyestuff of the constitution

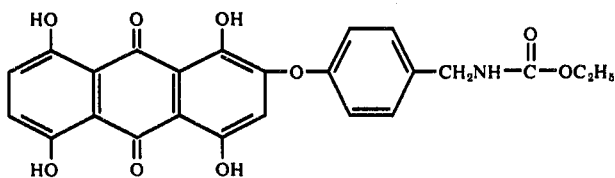

which dyes polyester fabric in yellowish-red shades with very good fastness to washing.

EXAMPLE 50

41 Parts acetonitrile or 59 parts acetamide are dissolved at 15° to 20° C in 800 parts 96% sulphuric acid. The mixture is cooled to 10° C and 60 parts dichlorodimethyl ether are added dropwise within 30 minutes. Stirring is effected for a further 15 hours at 15° to 20° C.

33 Parts 1-amino-2-phenoxy-4-hydroxyanthraquinone are dissolved in 400 parts 96% sulphuric acid, and 100 parts of the above sulphuric acid solution are added dropwise at 15° to 20° C within 30 minutes. The mixture is stirred for a further 18 hours at room temperature and discharged into ice, the precipitated dyestuff is filtered off with suction, washed neutral and dried, and 40 parts of the dyestuff described in Table 1, Example 2, are obtained.

EXAMPLE 51

30 Parts 1,8-dihydroxy-2-thiophenoxy-4,5-dinitroanthraquinone are dissolved at 5° – 10° C in 500 parts 96% sulphuric acid and then 23 parts methylolcaprolactam are added. The mixture is stirred for 15 – 20 hours at 10° – 15° C and discharged into ice and this is followed by filtering off with suction, washing neutral and drying; there are obtained 40 parts of the dyestuff of the constitution

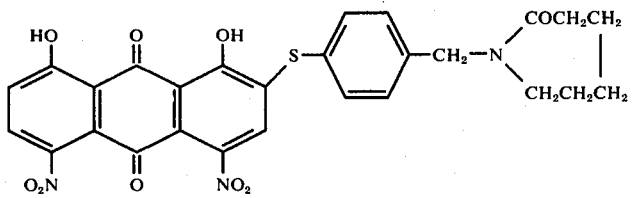

which dyes polyester fibres blue with very good fastnesses to wetting and sublimation.

EXAMPLE 52

25 Parts 1-amino-2-(4'-phenoxybutyloxy)-4-hydroxyanthraquinone are dissolved at 0° – 5° C in 400 parts 90% sulphuric acid, 15 parts methylolethylurethane are added and stirring is effected for 20 hours at 0° – 10° C. The mixture is then discharged into ice and the precipitated dyestuff is filtered off with suction, washed neutral and dried. There are obtained 31 parts of the dyestuff of the constitution

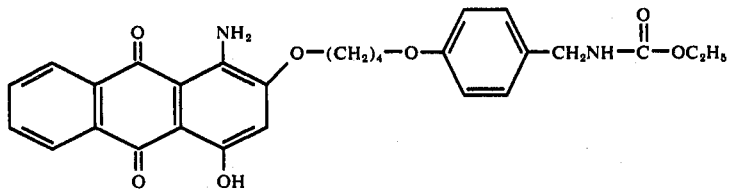

which dyes polyester materials red with very good fastness to sublimation.

EXAMPLE 53

25 Parts 1-amino-2-(2'-phenoxyethylthio-)-4-hydroxyanthraquinone are dissolved at 0° – 5° C in 400 parts 90% sulphuric acid, 20 parts methylolacetamide are added and stirring is effected for 20 hours at 0° – 5° C. The mixture is then discharged into ice and this is followed by filtering off with suction and washing neutral; after drying, there are obtained 28 parts of the dyestuff of the constitution

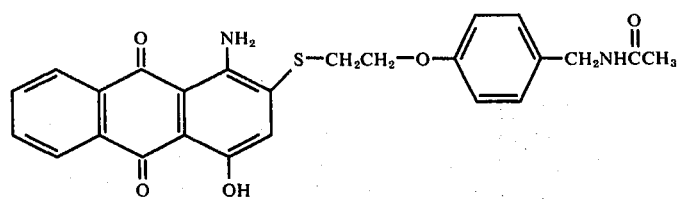

which dyes polyester materials bluish-red with very good fastness to sublimation.

EXAMPLE 54

30 Parts 1-amino-2-(2'-phenylaminoethoxy)-4-hydroxyanthraquinone are dissolved in 400 parts 96% sulphuric acid, and 20 parts methylolphthalimide are added. The mixture is stirred for 20 hours at room temperature and discharged into ice; the precipitated dyestuff is filtered off with suction, washed neutral and, after drying, there are obtained 35 parts of the dyestuff of the constitution

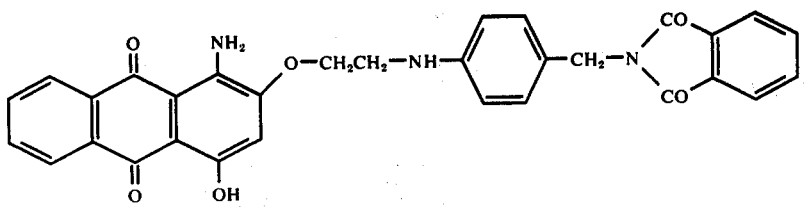

which dyes polyester materials red with very good fastnesses to wetting and sublimation.

EXAMPLE 55

35 Parts 1-amino-2-(tetrahydro-2'-oxynaphthyl)-4-hydroxyanthraquinone are dissolved at 0° – 10° C in 600 parts 96% sulphuric acid. 18 parts methylolmethacrylic acid amide are added, stirring is effected for a further 20 hours at 10° – 15° C and the mixture is discharged into ice. The precipitated dyestuff is filtered off with suction, washed neutral and dried, and there are obtained 43 parts of the dyestuff of the constitution

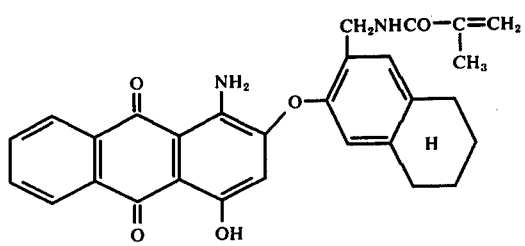

which dyes polyester materials red with very good fastnesses to wetting and sublimation.

EXAMPLE 56

40 Parts 1-amino-2-(4'-phenylphenoxy)-4-hydroxyanthraquinone are dissolved in 600 parts 96% sulphuric acid, and 19 parts methoxymethylurea are added at 5° – 10° C. Stirring is effected for 24 hours at room temperature and the mixture is discharged into ice and this is followed by filtering off with suction and washing neutral; after drying, there are obtained 48 parts of the dyestuff of the constitution

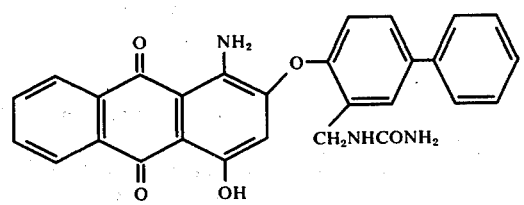

which dyes polyester materials red with good fastness to sublimation.

EXAMPLE 57

25 Parts of the anthraquinone

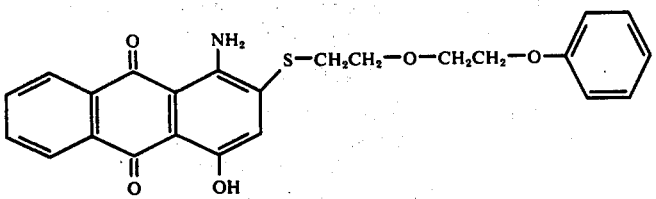

are dissolved in 450 parts 85% sulphuric acid, 10 parts methylolacetamide are added and stirring is effected for 20 hours at 0° – 5° C. The mixture is discharged into ice, and the precipitated dyestuff is filtered off with suction and washed neutral; after drying, there are obtained 31 parts of a dyestuff which dyes polyester fabric red with good fastness to sublimation.

EXAMPLE 58

30 Parts 1,4-diaminoanthraquinone-2-carboxylic acid chloride are suspended in 200 parts nitrobenzene, 30 parts 2-chloro-4-acetylamidomethylenephenol are added and heating is effected for 4 hours under reflux. The mixture is cooled, and the dyestuff which is formed is separated and washed several times with methanol; there are obtained 45 parts of a dyestuff of the constitution

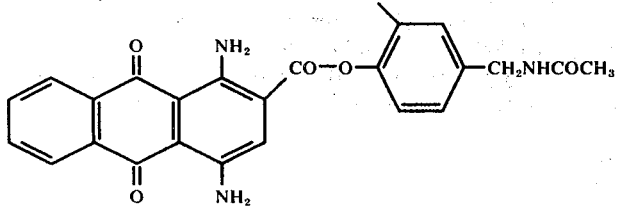

which dyes polyester materials in blue shades with good fastness to sublimation.

EXAMPLE 59

30 Parts 1,4-diaminoanthraquinone-2-carboxylic acid chloride are suspended in 200 parts nitrobenzene, 36 parts of the amine

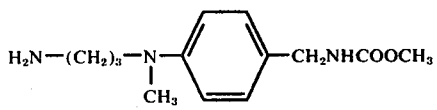

and 8 parts pyridine are added, and heating is effected for 5 hours under reflux. The dyestuff formed is separated, washed with methanol, and 51 parts of a blue dyestuff are obtained which dyes polyester materials in very good fastnesses to wetting and sublimation.

EXAMPLE 60

35 Parts 1,4-diaminoanthraquinone-2-sulphonic acid chloride are suspended in 200 parts chlorobenzene, 30 parts N-4'-hydroxybenzylcaprolactam and 8 parts pyridine are added and heating under reflux is effected for 3 hours. The mixture is cooled, the precipitated dyestuff is separated, and 55 parts of a dyestuff are obtained which dyes polyester fabric in blue shades with good fastnesses to wetting and sublimation.

EXAMPLE 61

30 parts, 1,4-diaminoanthraquinone-2-sulphonic acid chloride are suspended in 200 parts chlorobenzene, 34 parts 4'-acetylaminomethylenebenzylamine and 8 parts pyridine are added, and heating under reflux is effected for 2½ hours. The mixture is cooled, the precipitated dyestuffs is separated, and there are obtained 45 parts of a dyestuff of the constitution

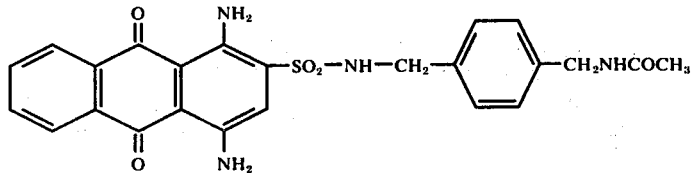

which dyes polyester fabric in blue shades with good fastnesses to wetting and sublimation.

What we claim is:

1. Dyestuff selected from the group consisting of

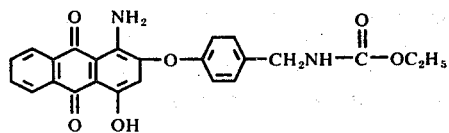

-continued

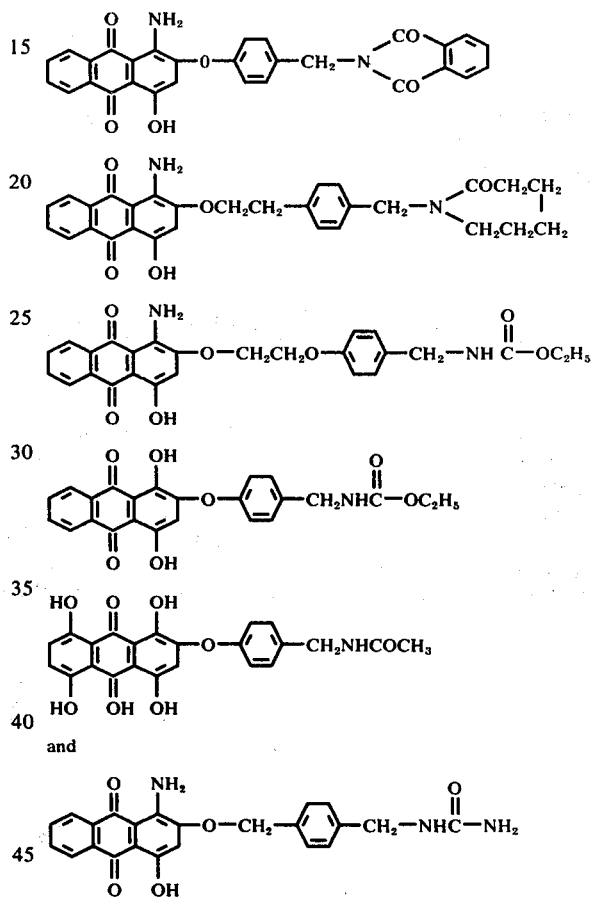

and

2. Dyestuff of claim 1 of the formula

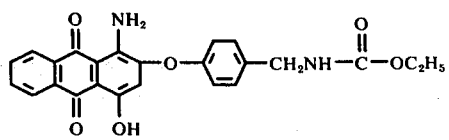

3. Dyestuff of claim 1 of the formula

4. Dyestuff of claim 1 of the formula
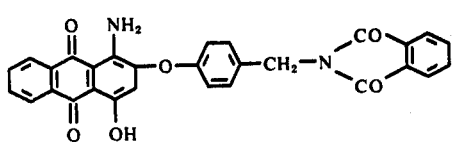
5. Dyestuff of claim 1 of the formula
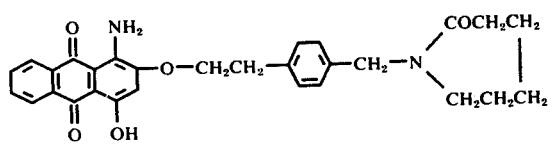
6. Dyestuff of claim 1 of the formula
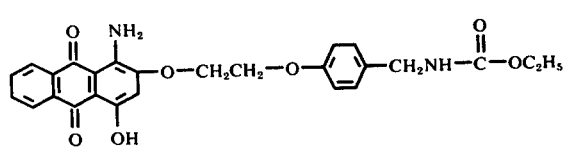
7. Dyestuff of claim 1 of the formula
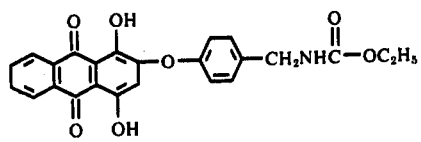
8. Dyestuff of claim 1 of the formula
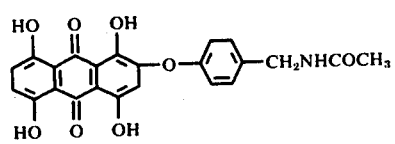
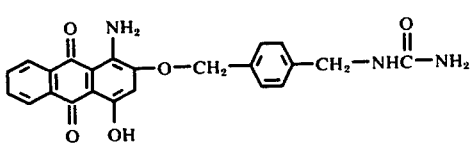
* * * * *